(12) United States Patent
Mis

(10) Patent No.: US 9,551,676 B2
(45) Date of Patent: Jan. 24, 2017

(54) SYSTEM AND METHOD FOR DETERMINING THE RADIOLOGICAL COMPOSITION OF MATERIAL LAYERS WITHIN A CONDUIT

(71) Applicant: University of Rochester, Rochester, NY (US)

(72) Inventor: Frederic J. Mis, Webster, NY (US)

(73) Assignee: University of Rochester, Rochester, NY (US)

( * ) Notice: Subject to any disclaimer, the term of this patent is extended or adjusted under 35 U.S.C. 154(b) by 267 days.

(21) Appl. No.: 14/527,543

(22) Filed: Oct. 29, 2014

(65) Prior Publication Data

US 2015/0139400 A1 May 21, 2015

Related U.S. Application Data

(60) Provisional application No. 61/897,271, filed on Oct. 30, 2013.

(51) Int. Cl.
*G01N 23/20* (2006.01)
*G21K 1/02* (2006.01)

(52) U.S. Cl.
CPC ......... *G01N 23/20091* (2013.01); *G21K 1/02* (2013.01); *G01N 2223/3035* (2013.01); *G01N 2223/316* (2013.01); *G01N 2223/628* (2013.01)

(58) Field of Classification Search
CPC ............... G01N 23/20091; G01N 2223/3035; G01N 2223/316; G01N 2223/628; G21K 1/02
See application file for complete search history.

(56) References Cited

U.S. PATENT DOCUMENTS

| | | | | |
|---|---|---|---|---|
| 3,506,832 A | * | 4/1970 | Struttman | G01T 7/02 250/505.1 |
| 5,038,033 A | * | 8/1991 | Carroll | G01V 5/06 166/247 |
| 5,239,568 A | * | 8/1993 | Grenier | A61B 6/4258 250/505.1 |
| 6,218,669 B1 | * | 4/2001 | Call | A61B 6/4258 250/336.1 |
| 6,242,744 B1 | * | 6/2001 | Soluri | G01T 1/161 250/363.02 |

\* cited by examiner

*Primary Examiner* — David Porta
*Assistant Examiner* — Shun Lee
(74) *Attorney, Agent, or Firm* — Robert D. Gunderman, Jr.; Patent Technologies, LLC

(57) ABSTRACT

There is provided a System and Method For Determining The Radiological Composition of Material Layers Within a Conduit. The system and method disclosed is equally applicable to pipes, vessels, and conduits as well as medical applications such as determining vessel thickness, occlusion, scarring, or the like in humans and animals. A phantom setup is disclosed that has a phantom containing a test standard such as a reactor water test standard, removable plates, a collimator and probe with a spectrometer display. The phantom setup provides a baseline data set that can be used in conjunction with field measurements to determine the composition of materials within the conduit, such as corrosion or the like. The baseline data set may be semilogarithmic and contains spectrometer readings of various plate thicknesses or quantities of plates.

19 Claims, 19 Drawing Sheets

SYSTEM AND METHOD FOR DETERMINING THE RADIOLOGICAL COMPOSITION OF MATERIAL LAYERS WITHIN A CONDUIT

CROSS REFERENCE TO RELATED PATENT APPLICATIONS

This application claims priority to U.S. Patent Application Ser. No. 61/897,271 filed Oct. 30, 2013 entitled "System And Method For Determining The Radiological Composition of Material Layers Within a Conduit" by Frederic J. Mis of Webster, N.Y., the entire disclosure of which is incorporated herein by reference.

BACKGROUND OF THE INVENTION

1. Field of the Invention

The present invention relates generally to measurement equipment and methods, and more particularly to a System and Method For Determining The Radiological Composition of Material Layers Within a Conduit.

2. Description of the Related Art

Determination of the radiological contamination layer within a conduit such as a light water reactor pipe in a nuclear power plant provides proper decision making regarding chemistry regimes to best minimize the radiological transportation of corrosion products and activation products. Corrosion products such as Co-58 and Co-60, and some fission products such as Cs-134 and Cs-137, are the primary causes of radiation exposure to plant workers during reactor maintenance. In addition, excessive corrosion on valves reduces their operational effectiveness. Once the make-up of the corrosion layer is understood, changes in plant water pH, clean up system alternatives, or operating temperatures may be made to reduce the continuous build up of corrosion products. Unfortunately, techniques and equipment currently used to measure the radiological contamination layer within pipes in a nuclear power plant are large, bulky, and difficult to maneuver into the sometimes tight, inaccessible, or elevated spaces within a nuclear power plant. What is needed is a measurement device and associated methods that is compact, lightweight, easy to operate, and provides quick and accurate readings of the radiological contamination layer within the conduit, pipe, or vessel.

It is thus an object of the present invention to provide a System and Method For Determining The Radiological Composition of Material Layers Within a Conduit such as a pipe or a vessel. Other objects of the present invention include, but are not limited to, determining vessel thickness, occlusion, scarring, or the like in human or animal bodies. These and other objects of the present invention are not to be considered comprehensive or exhaustive, but rather, exemplary of objects that may be ascertained after reading this specification with the accompanying drawings and claims.

BRIEF SUMMARY OF THE INVENTION

In accordance with the present invention, there is provided a system for determining the radiological composition of material layers within a conduit comprising a probe contained within a collimator; a spectrometer operatively connected to the probe; a phantom setup comprising a vessel containing a test standard, a plurality of removable plates, and a collimator probe attachment point; and a semi-logarithmic plot of spectrometer readings taken with various quantities of removable plates for comparison with field readings. Additionally, a source for field readings and a method for comparing the semi-logarithmic plot of spectrometer readings with the field readings are provided.

The foregoing paragraph has been provided by way of introduction, and is not intended to limit the scope of the invention as described by this specification and the attached drawings and claims.

BRIEF DESCRIPTION OF THE DRAWINGS

The invention will be described by reference to the following drawings, in which like numerals refer to like elements, and in which.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the invention as defined by this specification, claims and drawings attached hereto.

DESCRIPTION OF THE PREFERRED EMBODIMENTS

The use of gamma spectroscopy for measuring the radiological composition of material layers within a pipe is incomplete at best. While the thickness of the pipe and associated nuclear insulation is known, the composition and radioactivity of the corrosion layer within the pipe is not. A method and system to create and use a novel phantom setup in conjunction with a spectrometer provides the ability to determine the radiological composition of the corrosion layers within a pipe, something that was heretofore not attainable with spectrometers alone.

The System and Method For Determining The Radiological Composition of Material Layers Within a Conduit uses actual radioisotopes in known activity deposition, using NIST traceable activities, uniformly distributed in an extremely thin layer within a planar phantom. Steel plates are then added to create thicknesses that mimic the standard pipe thicknesses found in light water reactors. These thicknesses include ⅜ inch, 1.25 inch, 2.25 inch, and 2.75 inch. In addition, a layer of nuclear insulation is added to mimic those instances when measurements are made with insulation remaining on the pipe. The measurements that are taken are plotted using a semi-logarithmic scale, and are a straight line. The slope of the resulting line becomes a calibration factor which, based on the radioisotopes used, reflects the conditions within an enclosed system. This system is the first modeled, calibration system which provides actual attenuation, build up and scatter conditions that would affect real world systems.

Figure 1:
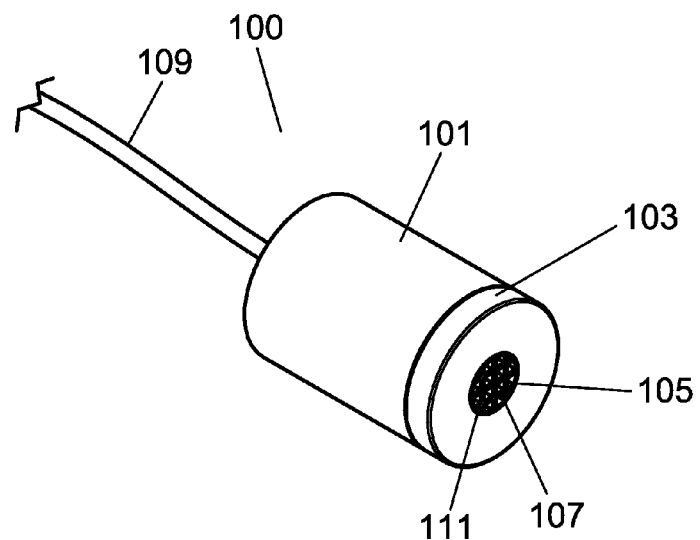
FIG. 1 is as perspective view of the collimator-probe of the present invention.

To take measurements in both the calibration environment using a phantom setup and in the field, a collimator-probe arrangement is disclosed. FIGS. 1-6 depict such a collimator probe of the present invention. FIG. 1 is a perspective view of the collimator-probe 100 of the present invention. A shielded housing 101 can be seen, which serves as a collimator having an opening to direct detected radiation towards a sensing face of a probe contained within the collimator. The shielded housing 101 may, in some embodiments of the present invention, be generally cylindrical. An example of suitable dimensions for a generally cylindrical shielded housing 101 is a cylinder that is approximately 8 centimeters tall with a diameter of 6 centimeters. The wall thickness of this exemplary cylinder is approximately 1.4 centimeters. The shielded housing 101 is made from a high density material such as lead, tungsten, depleted uranium, or the like to provide proper shielding. The shielded housing 101 is also covered with a material such as copper to allow for rapid decontamination. Such a covering is made by electroplating, forming of a suitable foil around the shielded housing, painting, or the like. Both the inside and the outside of the shielded housing 101 are covered with such a material. The shielded housing 101 may be cast, molded, machined, or otherwise formed into a generally hollow structure such as a cylinder that is capable of containing a probe, such as the probe 203 depicted in FIG. 2. In addition, a soft material such as a plastic sponge material may line the inside of the shielded housing 101 in order to secure the probe 203 (see FIG. 2) and keep it centered within the shielded housing 101. A removable cover 103 is fitted to the shielded housing 101 to allow for access to the probe contained within. The removable cover 103 may be made from a similar high density material as that which the shielded housing 101 is made from. Lead, tungsten or depleted uranium, for example, are suitable high density materials. The removable cover 103 is also covered with a material such as copper or a layer of tin and copper to allow for rapid decontamination. Such a covering is made by electroplating, forming of a suitable foil around the shielded housing, painting, or the like. The removable cover 103 may be cast, molded, machined, or otherwise formed. In some embodiments of the present invention, the removable cover 103 has a feature such as a recessed or beveled circumference that joins with a mating surface of the shielded housing 101 for proper retention thereof. Mating features between the removable cover 103 and the shielded housing 101 may also include threads, tabs, slots, pins, posts, sockets, and the like. The removable cover 103 is of a geometry that matches with the geometry of the shielded housing, for example circular. The removable cover 103 also has an opening 111 such as a circular opening that contains a spacer 105 and a grid 107. The opening 111 is sized to accommodate the face of the probe 203 (see FIG. 2), and may, in one embodiment of the present invention, be approximately 2.4 centimeters in diameter. The probe 203 (see FIG. 2) sits recessed in the opening 111, and may, for example, sit approximately 2 centimeters inward. The spacer 105 is fitted to the shielded housing 101 to keep the probe contained within the shielded housing 101 a constant distance from the opening 111 in the removable cover 103. The spacer may, in one embodiment of the present invention, be an open cylinder or otherwise annular in geometry. Fitted within or proximate to the spacer 105 is a grid 107. The grid 107 is made from a high density material such as lead, tungsten or depleted uranium, and prevents low energy lateral photons from hitting the face of the probe, which would result in incorrect readings. An example of a suitable grid 107 is a three by three matrix of lead plates where each plate is ¹⁄₁₆ inch thick and 1 centimeter deep. The lead plates are aligned to create a grid 107 such as that depicted in FIG. 2 where the grid 107 comprises a plurality of rectangular openings. The grid 107 may also be cast, machined, or otherwise fabricated such that a plurality of openings are created. The openings may be rectangular, square, circular, or the like. The spacer 105 and the grid 107 are retained in the opening 111 by use of glue, adhesives, solder, retainer rings, clips, or the like.

Figure 2:
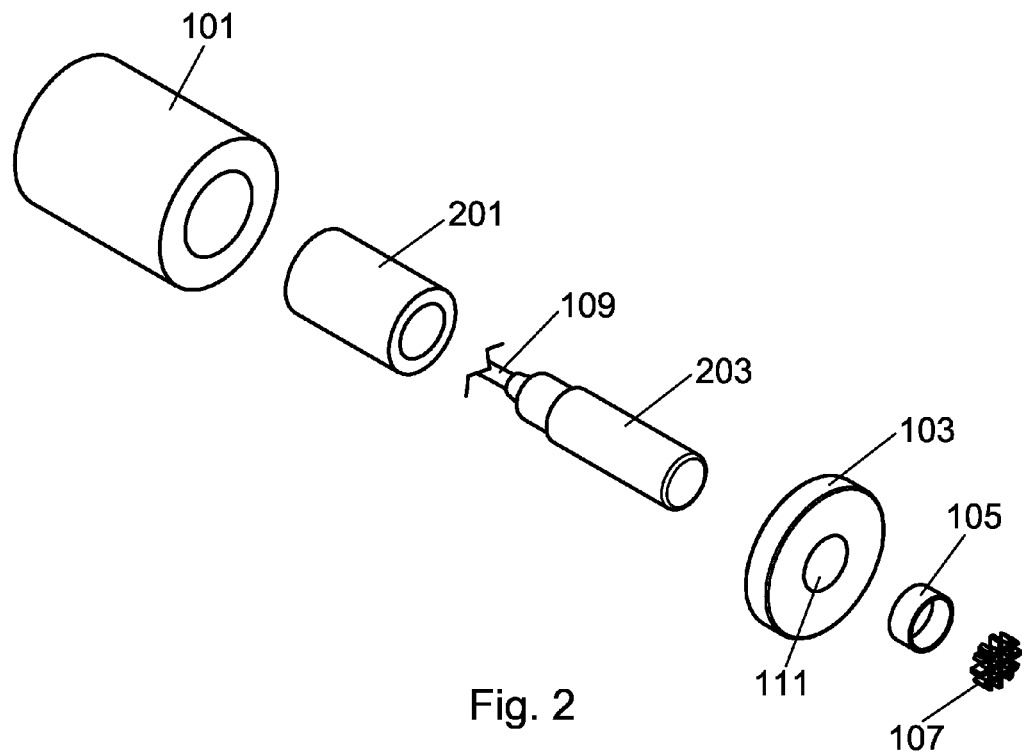
FIG. 2 is an exploded view of the collimator-probe of the present invention.

FIG. 2 depicts an exploded view of the collimator-probe of the present invention. The shielded housing 101 can be seen along with the removable cover 103, and the spacer 105 and grid 107. Also seen in FIG. 2 is the probe retainer 201 that may be generally cylindrical in shape and made from a soft material such as a low density polyethylene foam or the like. A low density material provides a low attenuation coefficient and is thus desirable to avoid erroneous readings.

In some embodiments of the present invention, the probe retainer 201 is secured only by friction, without the use of glue. Within the probe retainer 201 is the probe 203. A suitable probe is a cadmium Zinc Telluride (CZT) probe such as those made by Canberra of Meriden, Conn., USA. The CZT probes made by Canberra may also be used with their Inspector 1000 display. Various size probes are available based on the energy range of interest. A 500 mm$^2$ probe adequately monitors a maximum dose rate of 200 mrem/hr. A 60 mm$^3$ probe has an upper range of 1,000 mrem/hr. The probe 203 is positioned such that its sensing surface is facing outward through the opening 111.

Figure 3:
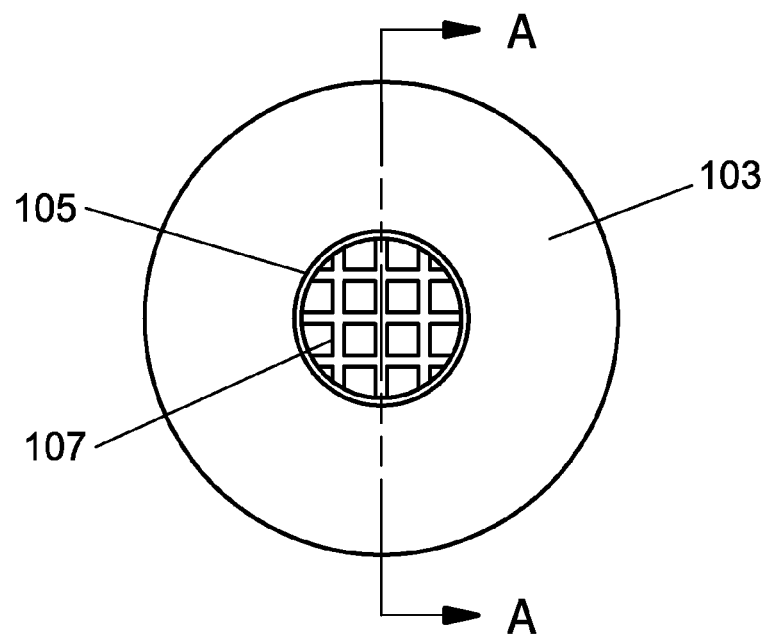
FIG. 3 is a front plan view of the collimator-probe of the present invention.

FIG. 3 is a front plan view of the collimator-probe of the present invention. The grid 107 can be seen with the sensing surface of the probe behind the grid 107.

Figure 4:
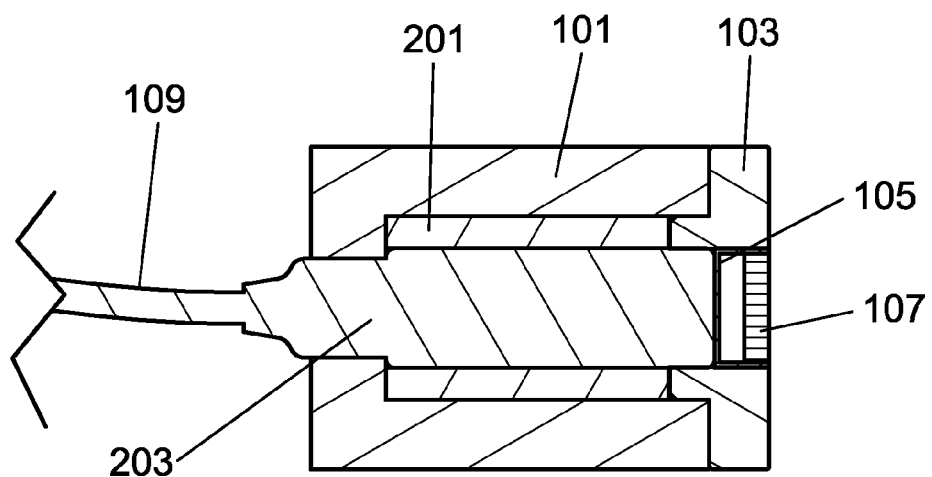
FIG. 4 is a cross sectional view of the collimator-probe of the present invention taken along line A-A of FIG. 3.

FIG. 4 is a cross sectional view of the collimator-probe of the present invention taken along line A-A of FIG. 3. The probe retainer 201 can be seen with the probe 203 centered there within. The spacer 105 can also be seen along with the shielded housing 101 and the removable cover 103. The removable cover 103 in the embodiment depicted in FIG. 4 has a flange that protrudes perpendicular to the inner surface of the removable cover 103 and is circumferential to the opening that contains the spacer 105 and grid 107, thus providing as secure fit to the shielded housing 101.

Figure 5:
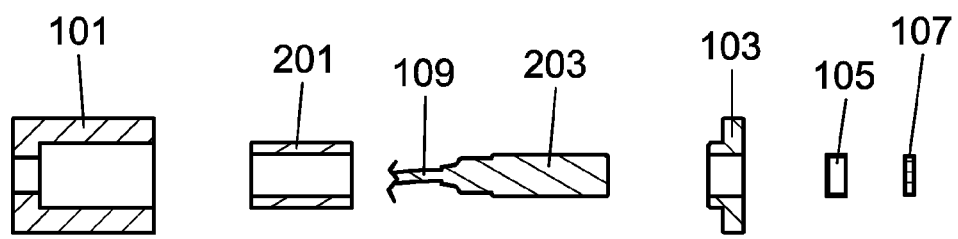
FIG. 5 is an exploded cross sectional view of the collimator-probe of the present invention taken along line A-A of FIG. 3.

FIG. 5 is an exploded cross sectional view of the collimator-probe of the present invention taken along line A-A of FIG. 3. The cable 109 that connects the probe 203 to a spectrometer display (not shown) can be seen along with an opening in the rear of the shielded housing 101 to accommodate the exit path of the cable 109.

Figure 6:
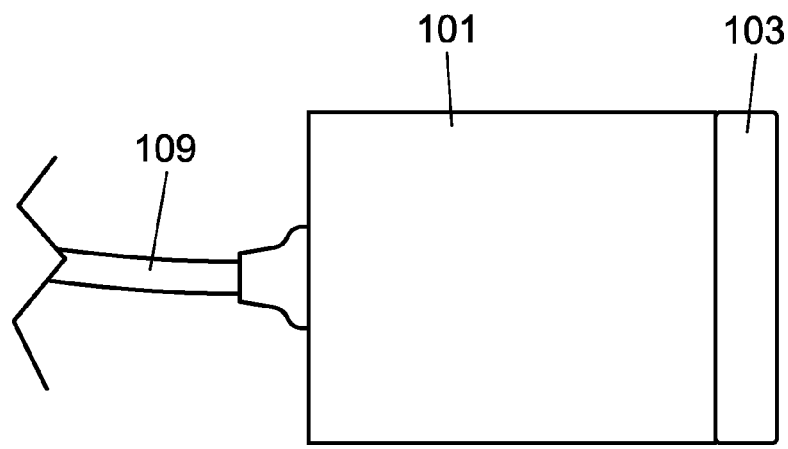
FIG. 6 is a top plan view of the collimator-probe of the present invention.

FIG. 6 is a top plan view of the collimator-probe of the present invention. The cable 109 can be seen protruding from the shielded housing 101. The opening in the rear of the shielded housing 101 is such that a tight fit between the shielded housing 101 and the cable 109 are provided.

Turning to FIGS. 7-11, a phantom setup 700 can be seen that creates a calibration standard through the use of a spectrometer that can be used in determining the radiological composition of the corrosion layers within a pipe.

Figure 7:
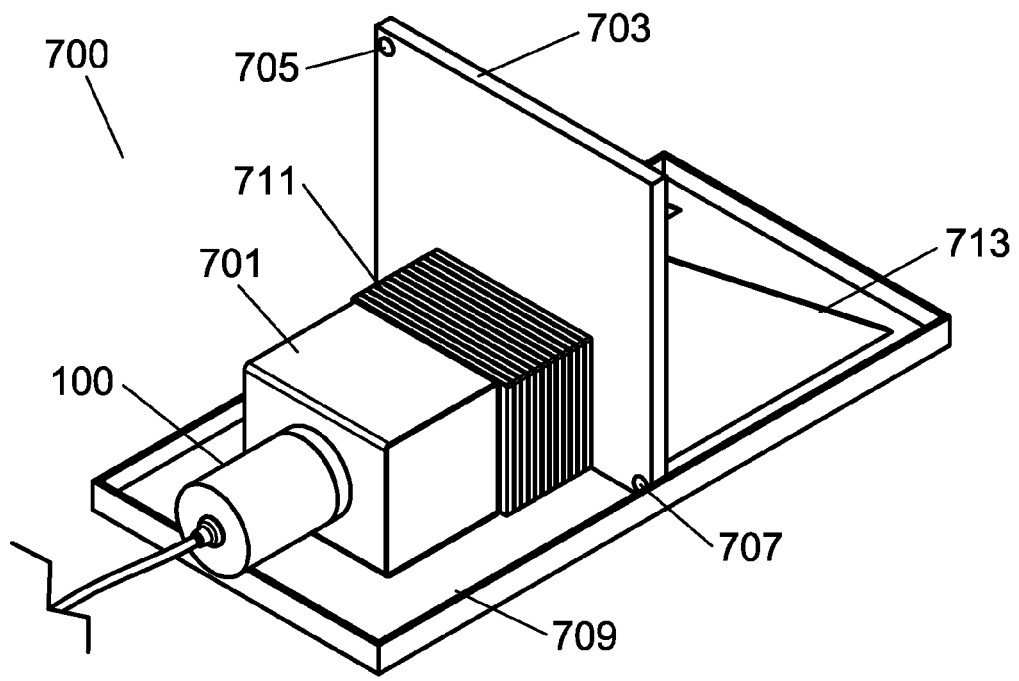
FIG. 7 is a perspective view of the phantom setup of the present invention.

FIG. 7 is a perspective view of the phantom setup 700 of the present invention. The collimator-probe 100, as previously described herein, can be seen. A vessel 703 such as a nuclear medicine phantom, is seen mounted to a base 709. The base 709 includes walls or edges to contain a spill should it occur. The base 709 may be made from a plastic such as polypropylene, acetyl, polycarbonate, or a metal such as stainless steel or the like. The vessel 703 may be made from a plastic such as polycarbonate or the like. A first fill/vent plug 705 and a second fill/vent plug 707 are fit to the vessel 703 in a manner that provides a leak free seal. Threaded fittings with a gasket, friction fittings with a gasket, or the like may be used. The vessel 703 may, in one embodiment, be rectangular, and may, by example, be 26 inches×16 inches×0.5 inches internal volume. The vessel 703 is configured in the vertical position, and may contain a radioactive water mix, such as, for example, 600 cubic centimeters of liquid including 2 cubic centimeters of Co-60 (containing 65.5 uCi), and 2 cubic centimeters of Cs-137 (containing 72.7 uCi) with the balance being, for example, water. The vessel 703 may be, in one embodiment, 1 centimeter thick with 600 square centimeters of exposure surface area. Placed between the collimator-probe 100 and the filled vessel 703 is a series of plates 711 and also insulation 701. The series of plates 711 comprise steel plates of a given thickness, for example, 0.25 inches. The series of plates 711 may comprise, for example, 12 total plates, each of 0.25 inches thickness, for a total starting thickness of 3 inches. The insulation 701 represents a typical thickness of nuclear insulation. A first gusset 713 and a second gusset 801 (see FIG. 8) may be employed to secure the vessel 703 in a proper upright position, as depicted in FIG. 7. With the phantom setup described, readings may be taken at incremental plate thicknesses by removing or adding plates for each reading. In addition, readings with and without the nuclear insulation 701 are taken.

Figure 8:
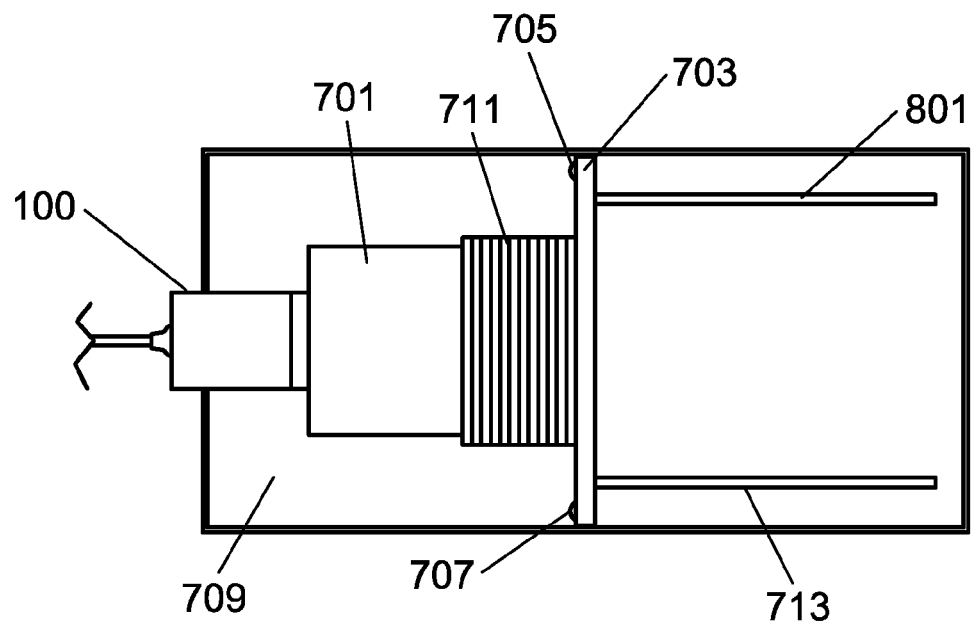
FIG. 8 is a to plan view of the phantom setup of the present invention.

FIG. 8 is a top plan view of the phantom setup of the present invention depicting the vessel 703 containing the activity source and the collimator-probe taking readings through the plates 711 and insulation 701.

Figure 9:
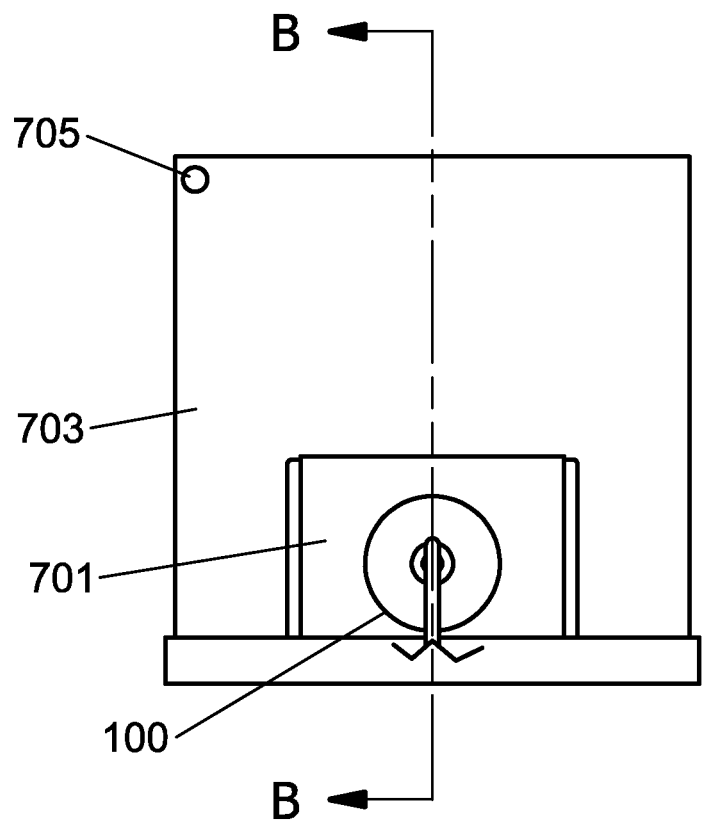
FIG. 9 is a rear plan view of the phantom setup of the present invention.

FIG. 9 is a rear plan view of the phantom setup of the present invention that shows the orientation of the vessel 703 in relation to the collimator-probe 100, plates 711 and insulation 701.

Figure 10:
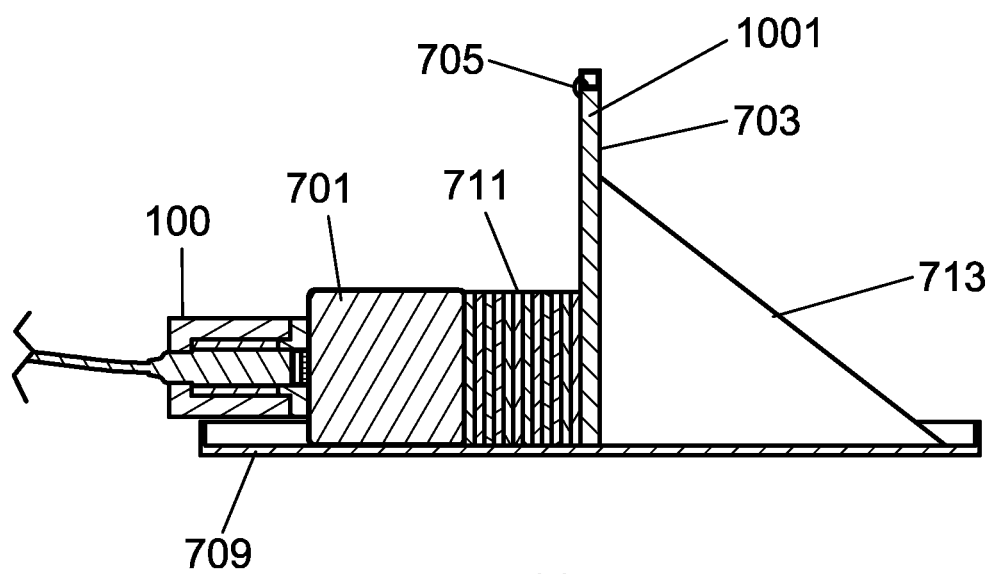
FIG. 10 is a cross sectional view of the phantom setup of the present invention taken along line B-B of FIG. 9.

FIG. 10 is a cross sectional view of the phantom setup of the present invention taken along line B-B of FIG. 9. In cross section, the reactor water test standard 1001 can be seen. A reactor water test standard 1001 may include, for example, 600 cubic centimeters of water, 2 cubic centimeters of Co-60 (containing 65.5 uCi), and 2 cubic centimeters of Cs-137 (containing 72.7 uCi).

Figure 11A:
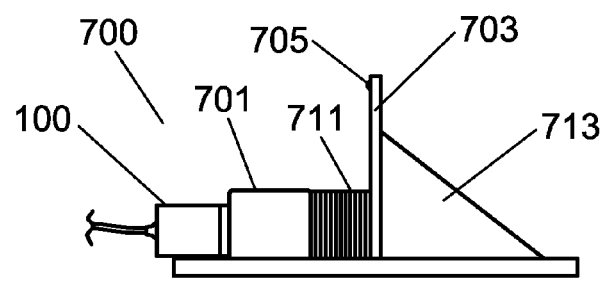
FIGS. 11A-11N depict the phantom setup in use with sequential removal or addition of plates and insulation.
Figure 11B:
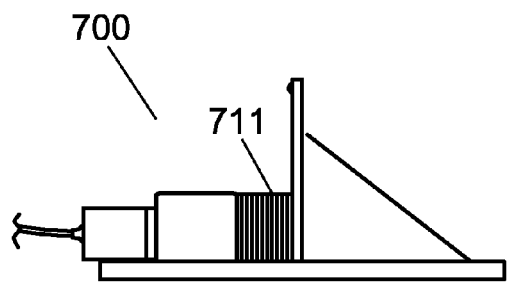
Figure 11C:
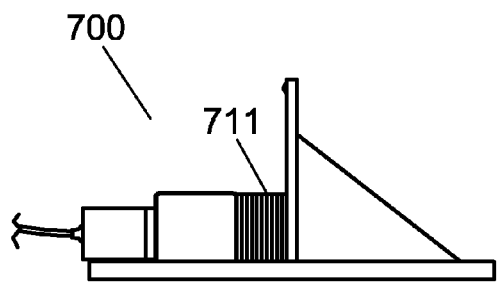
Figure 11D:
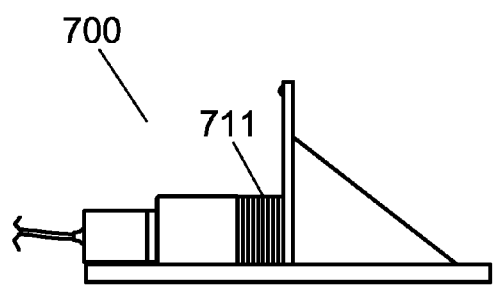
Figure 11E:
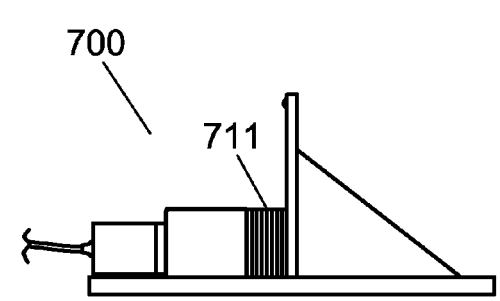
Figure 11F:
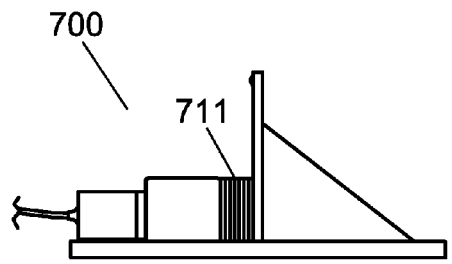
Figure 11G:
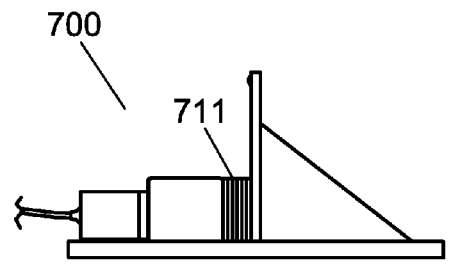
Figure 11H:
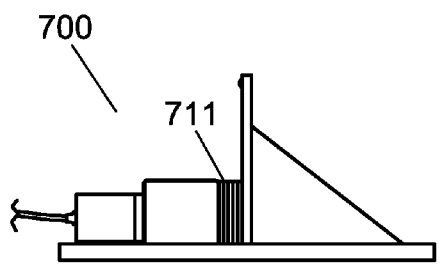
Figure 11I:
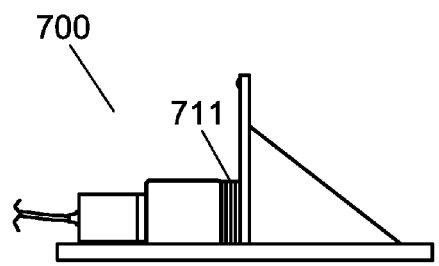
Figure 11J:
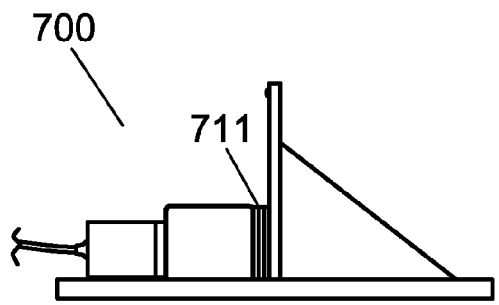
Figure 11K:
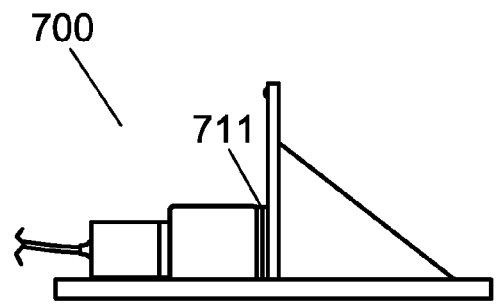
Figure 11L:
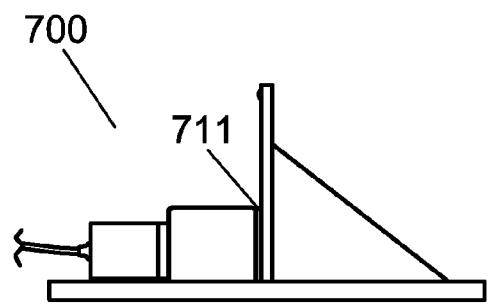
Figure 11M:
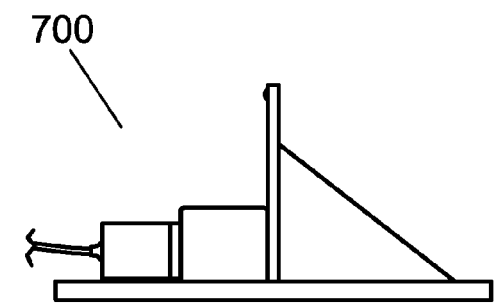
Figure 11N:
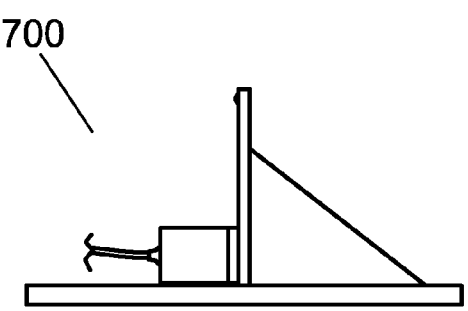

FIGS. 11A-11N depict the phantom setup in use with sequential removal or addition of plates and insulation. In FIG. 11A, all plates and the insulation are in place. FIG. 11B depicts one plate removed, FIG. 11C depicts two plates removed, FIG. 11D depicts three plates removed, and so on. FIG. 11L thus depicts one plate remaining, and FIG. 11M depicts no plates remaining, only insulation. Lastly, FIG. 11N depicts no plates or insulation between the collimator-probe and the vessel. For each step portrayed in FIGS. 11A-11N, a radioisotopic activity reading is taken and recorded. A plot of $\log_{(10)}$ of activity vs. steel thickness in 0.25 inch increments (or the appropriate units) is then prepared. The plot can then be used in removing "the confounder" when taking field measurements of radiological sedimentation in pipes.

Now when field measurements of radioisotopic activity are taken to determine the radiological sedimentation present within a pipe, the plot of $\log_{(10)}$ of activity vs. steel thickness can be used to remove the unknown variables and obtain true and accurate readings. FIGS. 12-15 depict such field measurements.

Figure 12:
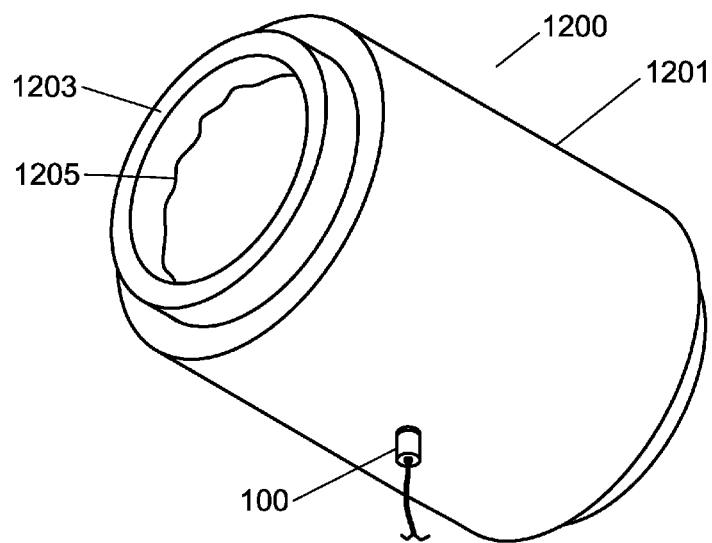
FIG. 12 is a perspective view of a typical field setup of the present invention showing the collimator-probe attached to an insulated pipe.

FIG. 12 is a perspective view of a typical field setup 1200 of the present invention showing the collimator-probe attached to an insulated pipe. The collimator-probe 100 is held up to the insulation 1201 of a pipe 1203. The corrosion layer 1205 and associated activity from the corrosion layer is an unknown, and is measured through a known pipe thickness and pipe insulation thickness. Field readings are taken and adjusted by using the plot of $\log_{(10)}$ of activity vs. steel thickness in the previously described, phantom calibration measurements.

Figure 13:
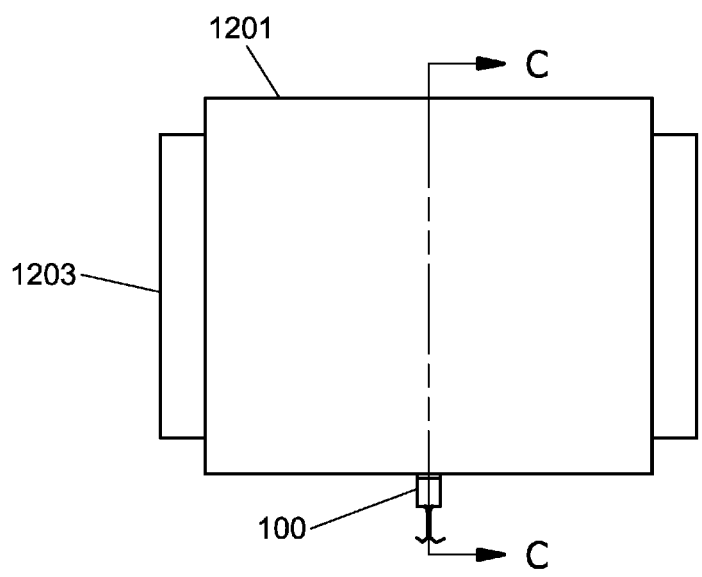
FIG. 13 depicts a plan view of a typical field setup of the present invention showing the collimator-probe attached to an insulated pipe.

FIG. 13 depicts a plan view of as typical field setup of the present invention showing the collimator-probe attached to an insulated pipe.

Figure 14:
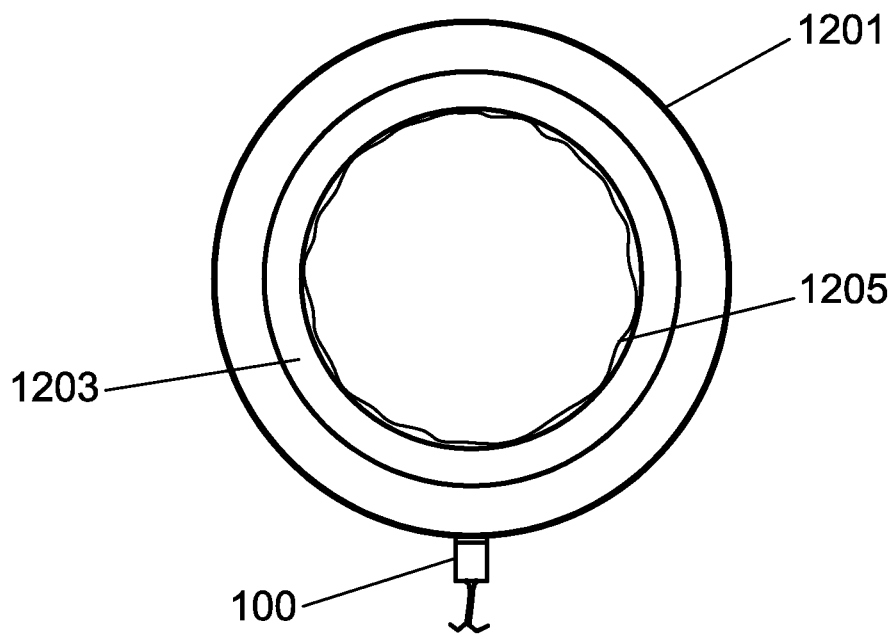
FIG. 14 depicts an end view of a typical field setup of the present invention showing the corrosion layer within an insulated pipe.

FIG. 14 depicts an end view of a typical field setup of the present invention showing the corrosion layer within an insulated pipe.

Figure 15:
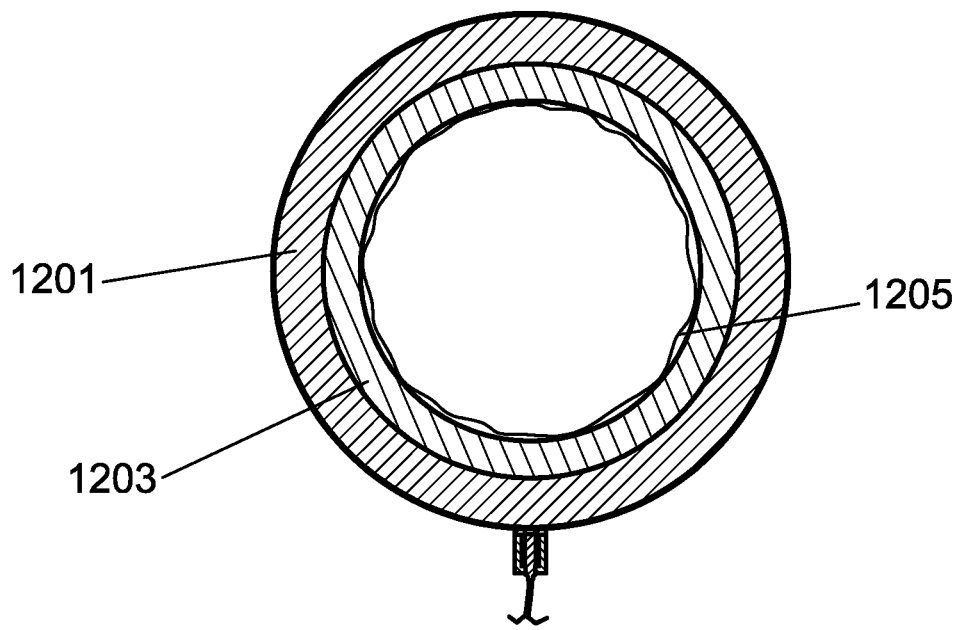
FIG. 15 depicts a cross sectional view of the insulated pipe taken along line C-C of FIG. 13.

FIG. 15 depicts a cross sectional view of the insulated pipe taken along line C-C of FIG. 13.

Figure 16:
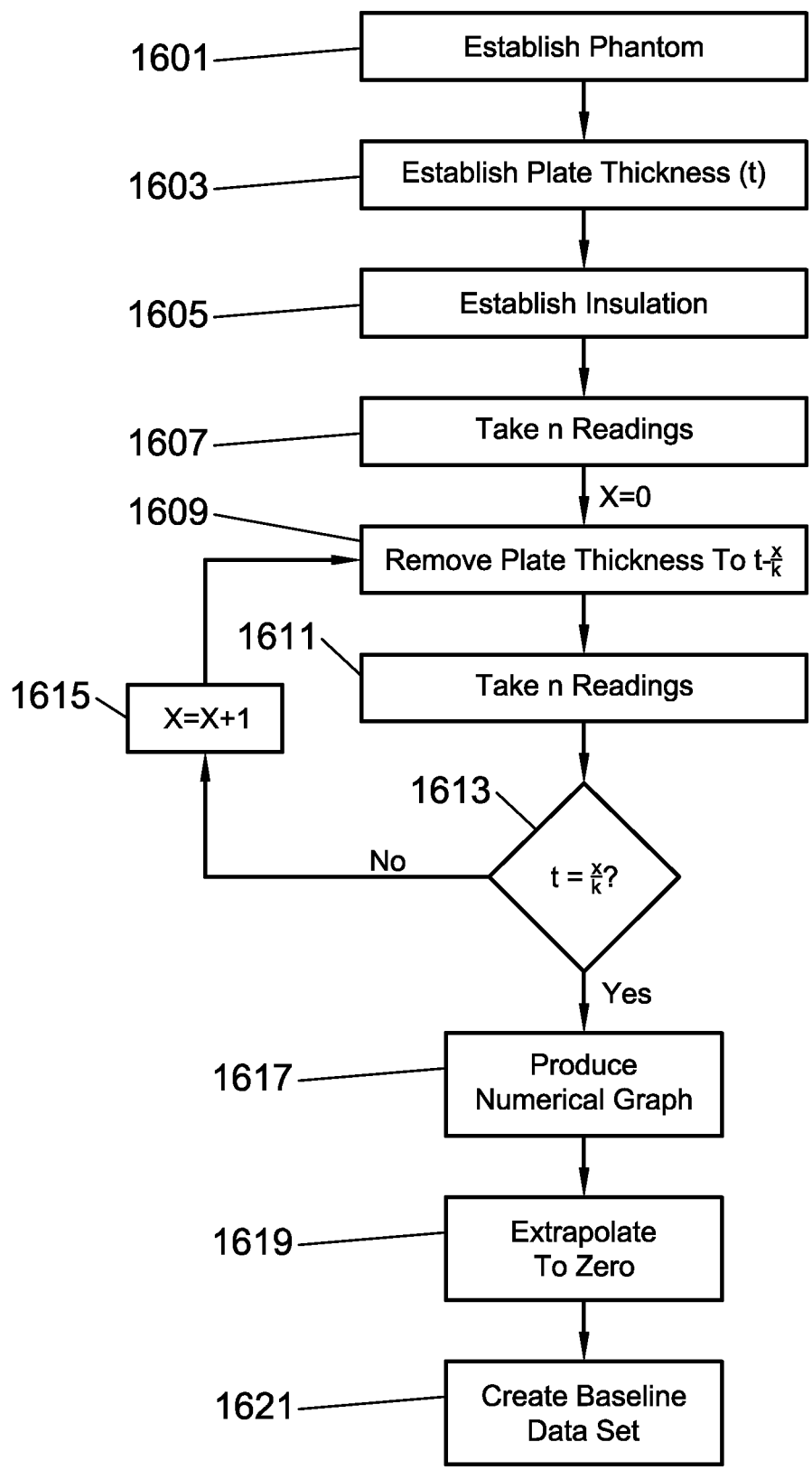
FIG. 16 is a flowchart of a method of establishing a baseline using the phantom setup.

FIG. 16 is a flowchart of a method of establishing a baseline using the phantom setup. In step 1601, the phantom is established. This involves preparing the phantom setup 700 as previously described herein. Once the phantom is established and ready for measurements, the plate thickness (t) is determined in step 1603 by adding the total number of plates in the setup, for example, eleven ¼ inch plates, for a total thickness of 2.75 inches. The plates may be, for example, steel plates. In step 1605, insulation is established. A layer of nuclear insulation of a known thickness and material is added. In step 1607, n readings are taken. For example three readings, one of Cs-134, one of Cs-137 and one of Co-60. In step 1609, one plate is removed, n readings are again taken, the plate thickness is decreased in step 1609 to a thickness of t−x/k where x is a counter that is incremented by one in step 1615 and k is the inverse of the plate thickness per plate. For example, with ¼ inch plates k is equal to 4. After each decrement in step 1615, it readings are taken in step 1611, and step 1613 determines if the final plate has been removed by determining if the overall thickness, for example, 2.75 inches, equals the current value of x (for example, 11) divided by k (for example 4). If the answer is no, the plates will continue to be decremented and n readings taken until such time as t=x/k. In step 1617, a numerical graph is produced, in step 1619 the graph is extrapolated to zero, and in step 1621 as baseline data set is created to be used to remove the confounder in subsequent field measurements, as previously described herein. The graph is typically plotted using a semi-logarithmic scale, and is a straight line. The slope of the resulting line becomes a calibration factor which, based on the radioisotopes used, reflects the conditions within an enclosed system.

Figure 17:
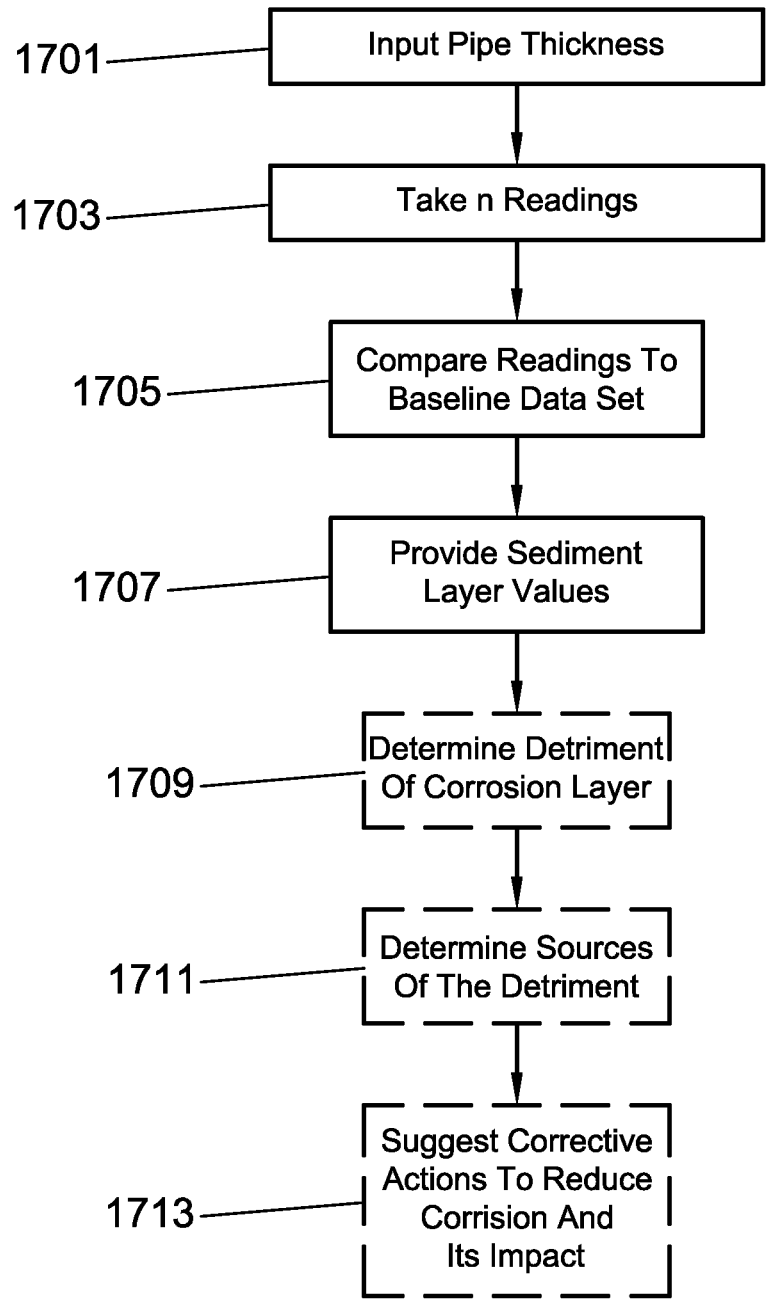
FIG. 17 is a flowchart of a method of determining the radiological composition of a material layer within a pipe.

FIG. 17 is a flowchart of a method of determining the radiological composition of a corrosion layer within a pipe. Once the phantom setup has produced a baseline data set or sets, field measurements may be taken to accurately determine the radiological composition of a corrosion layer within a pipe. In step 1701, the thickness of the pipe is input. In step 1703, n reading's are taken that are dependent on the source materials of interest. Once the readings are taken in step 1703, in step 1705 the readings are compared to the baseline data set from the phantom measurements described previously. This comparison removes the pipe, insulation, and other confounding attenuation factors from the measurements, providing sediment layer values in step 1707. Optionally, in step 1709, the detriment of the corrosion layer is determined, and in optional step 1711 the sources of the detriment are determined. In addition, in step 1713 optionally corrective actions are suggested to reduce corrosion and its impact. It should be noted that the steps performed herein may be manually performed, or they may be embodied in a computer program on a computer or on any device having, a processor including meters, probes, gauges, or other such instrumentation.

Having described an exemplary system and method for determining the radiological composition of material layers within a conduit, one can envision various embodiments thereof. These embodiments are to be considered within the spirit and broad scope of the present invention. For example, FIGS. 18-29 depict an alternate embodiment of the collimator-probe and provide examples of accessories that can be employed to facilitate convenience of use and the like. The shielded housing in this example is split in two halves that mate together and are held by fixturing such as clamps, straps, screws, bolts, or the like. It is important to note that the mating surfaces of each half should preferably have relief, angles, or other geometric changes to ensure proper shielding.

Figure 18:
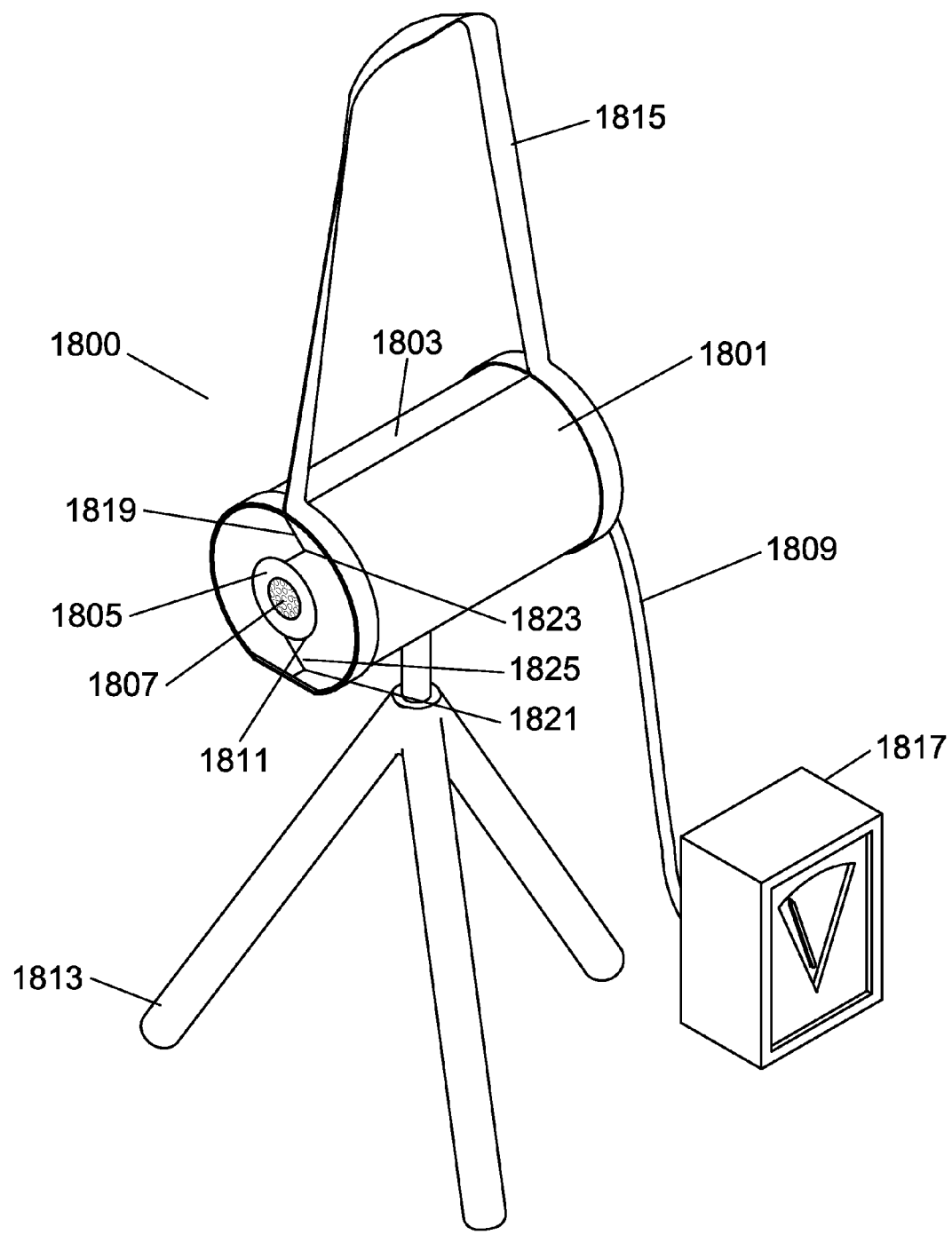
FIG. 18 depicts a perspective view of an alternate embodiment of the collimator-probe of the present invention with accessories.

FIG. 18 depicts a perspective view of an alternate embodiment of the collimator-probe of the present invention with accessories. The shielded housing depicted is generally cylindrical, and may in some embodiments have a flattened bottom portion to facilitate placement of the collimator-probe on a flat work surface or floor. An example of suitable dimensions for a generally cylindrical shielded housing is a cylinder that is approximately 8 centimeters tall with a diameter of 6 centimeters. The wall thickness of this exemplary cylinder is approximately 1.4 centimeters. The shielded housing is made from a high density material such as lead, tungsten, depleted uranium, or the like to provide proper shielding. The shielded housing is also covered with a material such as copper to allow for rapid decontamination. Such a covering is made by electroplating, forming of a suitable foil around the shielded housing, painting, or the like. Both the inside and the outside of the shielded housing are covered with such a material. The shielded housing may be cast, molded, machined, or otherwise formed into a generally hollow structure such as a cylinder that is capable of containing a probe, such as the probe 2201 depicted in FIG. 22. In addition, a soft material such as a plastic sponge material may line the inside of the shielded housing in order to secure the probe 2201 (see FIG. 22) and keep it centered within the shielded housing. In the case of this alternate embodiment, the shielded housing is made in two parts, a first half 1801 and a second half 1803, as depicted in FIGS. 18-29. To facilitate not only proper alignment of the two halves, but also proper shielding, each half has a feature such as a mating surface that may include protrusions, channels, slots, wedges, threads, tabs, pins, posts, sockets, and the like. In the example depicted, the first half of the shielded housing 1801 has a first channel 1823 and a second channel 1825 that each lie along a peripheral wall of the first half 1801 where each channel is generally parallel to the cylindrical axis that is formed with the joining of the first half and the second half to create a cylinder. The channels may take various geometries. In the example depicted, the channels are triangular, but may, in some embodiments, be square, rectangular, round, elliptical, octagonal, hexagonal, or the like.

On the second half of the shielded housing 1803, a first protrusion 1819 and a second protrusion 1821 can be seen. Each of these protrusions mates with the related channel on the first half of the shielded housing 1801, and similar to the related channels, each protrusion lies along a peripheral wall of the second half 1803 where each protrusion is generally parallel to the cylindrical axis that is formed with the joining of the first half and the second half to create a cylinder. The protrusions may take various geometries. In the example depicted, the protrusions are triangular, but may, in some embodiments, be square, rectangular, round, elliptical, octagonal, hexagonal, or the like.

Figure 22:
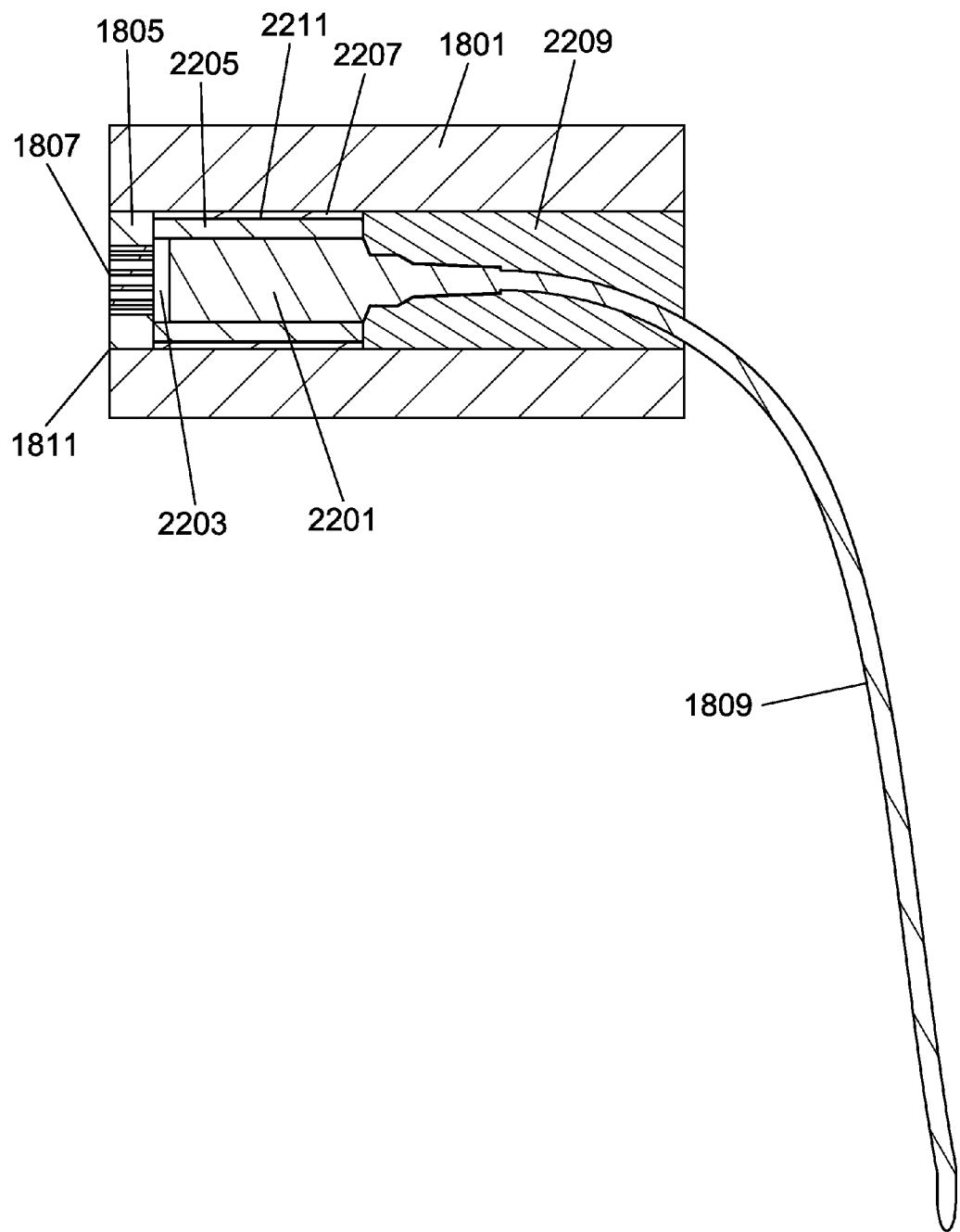
FIG. 22 is a cross-sectional view of the collimator-probe taken along line D-D of FIG. 21.

The two halves of the shielded housing retain a probe (depicted as 2201 in FIG. 22). The two halves are joined together such that the probe and related cable 1809 are properly placed and secured in the respective cavity of each half. The cable 1809 exits the joined together shielded housing through a channel in each half with a radius of curvature of each channel sufficient to prevent kinking or other maladies of the cable and probe assembly. The cable 1809 connects the probe to instrumentation 1817 such as a spectrometer. In FIG. 18, a carry strap 1815 can be seen with integral joining straps that traverse the perimeter of the shielded housing to retain the two halves together. These straps may be the only means of retaining the two halves, or alternatively or in combination, clamps, screws, bolts, rivets, or other such hardware may be employed. The straps may be made from as nylon, polypropylene, leather, or the like. It can be seen in FIG. 18 that the exemplary cylindrical shielded housing has a flattened bottom portion to allow placement on a flat surface without rolling. In addition, in some embodiments of the present invention, tripod fixturing such as a threaded insert may be added to allow use of the collimator-probe with a tripod 1813 or other such support structure.

Once a probe is installed in the shielded housing and the two halves are placed together and retained, one can see an opening 1811 in the resulting shielded housing. The opening 1811 may be of various geometries, but is depicted as a round opening in this example. This opening provides for detection capabilities for the probe contained within the shielded housing. To prevent low energy lateral photons from hitting the face of the probe, a grid 1807 is placed and secured within the opening 1811. The grid 1807 is made from a high density material such as lead, tungsten or depleted uranium and prevents low energy lateral photons from hitting the face of the probe, which would result in incorrect readings. An example of a suitable grid is a three by three matrix of lead plates where each plate is 1/16 inch thick and 1 centimeter deep. The lead plates are aligned to create a grid that comprises a plurality of openings. The grid 1807 may also be cast, machined, or otherwise fabricated such that a plurality of openings are created. The openings may be rectangular, square, circular, or the like. A spacer 1805 and the grid 1807 are retained in the opening 1811 by use of glue, adhesives, solder, retainer rings, clips, or the like.

Figure 19:
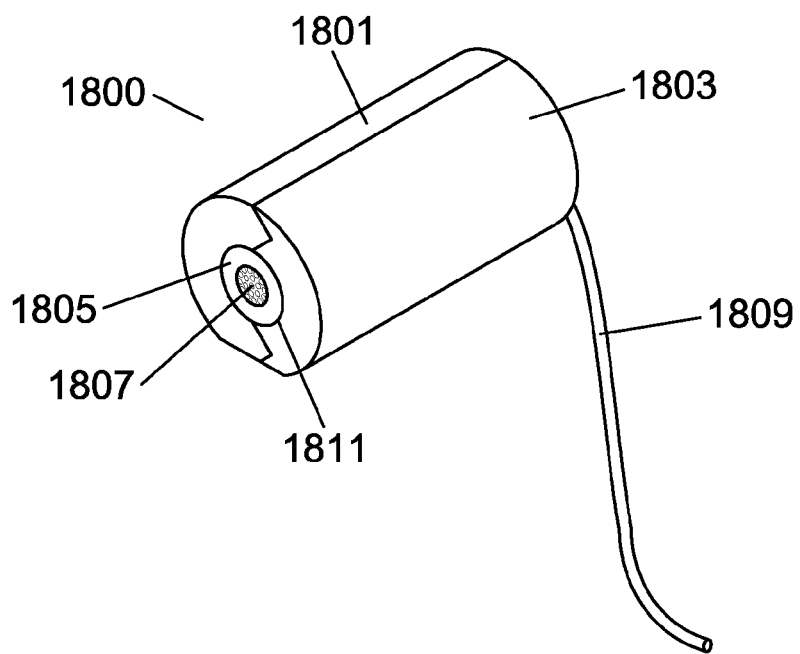
FIG. 19 depicts a perspective view of the alternate embodiment of the collimator-probe of FIG. 18.

FIG. 19 depicts a perspective view of the alternate embodiment of the collimator-probe of FIG. 18. The mating halves can be clearly seen in the assembled and operational position. The probe is contained within the shielded enclosure formed from the two halves. The mating protrusion and channel arrangement can be seen along with a flattened portion of the cylinder to prevent rolling or movement of the unit when placed on a surface, of which some embodiments of the present invention may employ.

Figure 20:
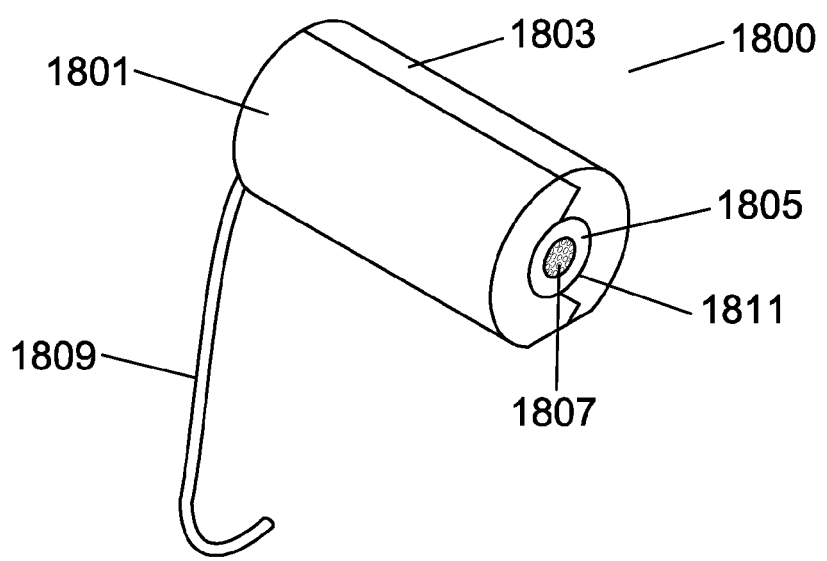
FIG. 20 is an opposite side perspective view of the alternate embodiment of the collimator-probe of FIG. 18.

FIG. 20 is an opposite side perspective view of the alternate embodiment of the collimator-probe of FIG. 18 showing similar attributes to the side depicted in FIG. 19.

Figure 21:
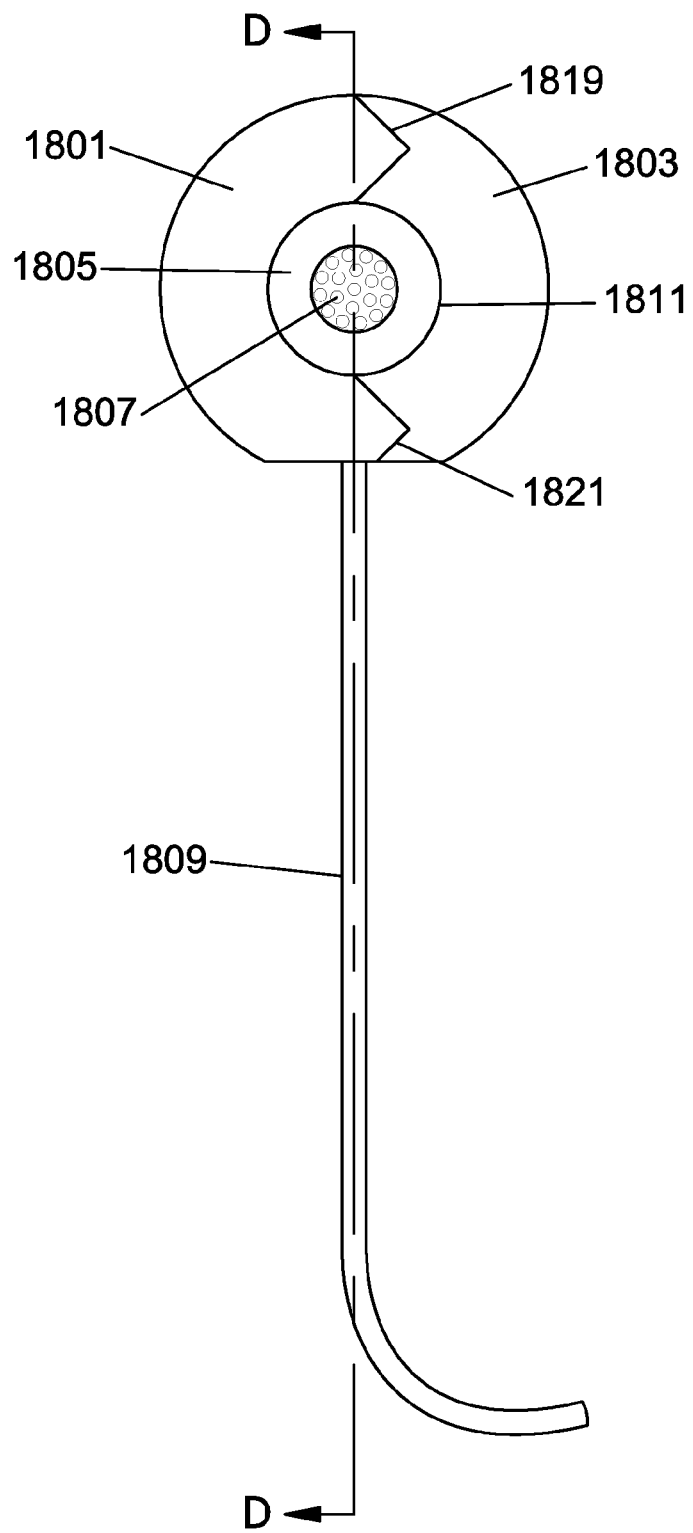
FIG. 21 is a front plan view of the collimator-probe of FIG. 18.

To clearly show the protrusion and channel arrangement of the first half of the shielded housing 1801 and the second half of the shielded housing 1803, FIG. 21 portrays a front plan view of the collimator-probe of FIG. 18. The grid 1807 and opening 1811 can also be clearly seen, the grid 1807 depicted herein by example and not limitation comprising a plurality of circular holes. In some embodiments of the present invention, the grid 1807 may comprise holes, openings or apertures that are square, rectangular, oval, hexagonal, octagonal, or the like. The spacer 1805 may be made from various materials, geometric shapes, or may, in some embodiments of the present invention, be omitted entirely. Further, in some embodiments of the present invention the grid 1807 may be integral with the shielded housing or a portion or a half thereof.

FIG. 22 is a cross-sectional view of the collimator-probe taken along line D-D of FIG. 21 where the inner structure of the shielded housing can be seen. In some embodiments of the present invention, the inner structure depicted in FIG. 22 is common to both the first half of the shielded housing 1801 and the second half of the shielded housing 1803. The structure depicted in FIG. 22 may be formed or made by casting, machining, cutting, grinding, heat forming, laser cutting or etching, chemical processes such as etching, and the like. The probe 2201 can be seen occupying a cavity that is similar in shape to that of the probe 2201. For clarity, the internal structure of the probe 2201 is not depicted. An air gap 2203 can be seen between the face of the probe and the grid 1807. The air gap 2203 may also, in some embodiments of the present invention, be occupied by a material such as a foam, a plastic, various spacers, or the like to provide, for example, structural definition to the air gap 2203. Further, in some embodiments of the present invention, the thickness of the air gap 2203 is zero or thereabouts, essentially meaning that there is no air gap 2203, or one that is minimal. A probe retainer 2205 may also be employed in some embodiments of the present invention to provide for adequate cushioning, conformal fit and retention of the probe 2201. The probe retainer 2205 is made from a soft material such as a low density polyethylene foam or the like. A low density material provides a low attenuation coefficient and is thus desirable to avoid erroneous readings. In some embodiments of the present invention, the probe retainer 2205 is secured only by friction, without the use of glue. Within the probe retainer 2205 is the probe 2201. A suitable probe is a cadmium Zinc Telluride (CZT) probe such as those made by Canberra of Meriden, Conn., USA. The CZT probes made by Canberra may also be used with their Inspector 1000 display. Various size probes are available based on the energy range of interest A 500 mm$^3$ probe adequately monitors a maximum dose rate of 200 mrem/hr. A 60 mm$^3$ probe has an upper range of 1,000 mrem/hr. The probe 2201 is positioned such that its sensing surface is facing outward through the opening 1811.

While a probe retainer 2205 may not be necessary in all situations and embodiments of the present invention, it may in some cases be useful and beneficial. A cadmium layer 2207 can also be seen which is in turn covered by a copper layer 2211 or a layer of tin and copper to allow for rapid decontamination. Such a layer is made by electroplating, forming of a suitable foil around the shielded housing, painting, or the like. The shielded housing itself is made from a shielding material 2209 such as lead, tungsten, depleted uranium or the like.

Figure 23:
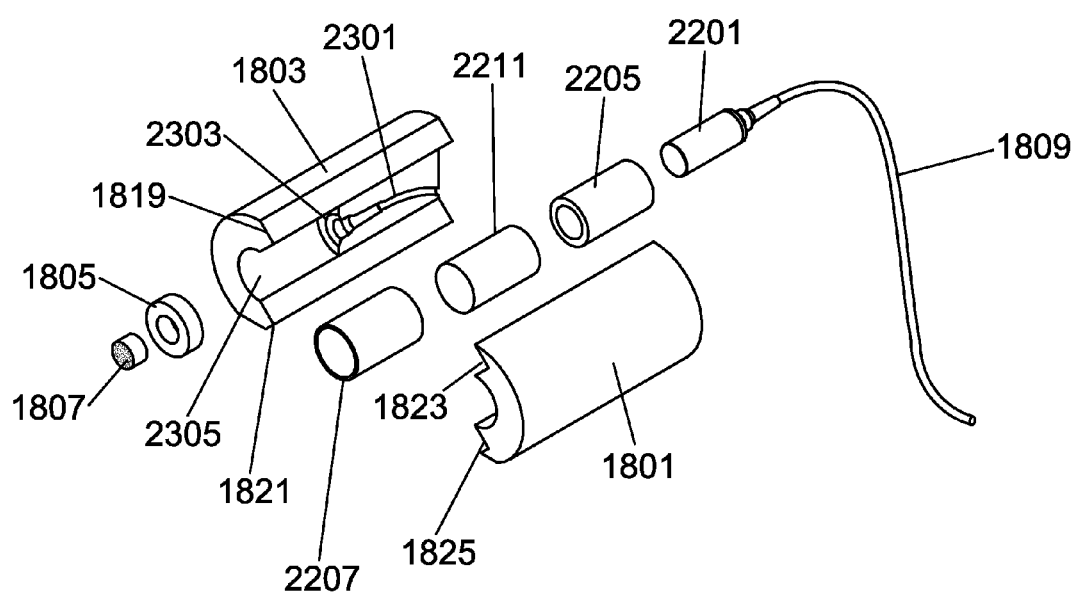
FIG. 23 is an exploded view of the collimator-probe of FIG. 18.
Figure 24:
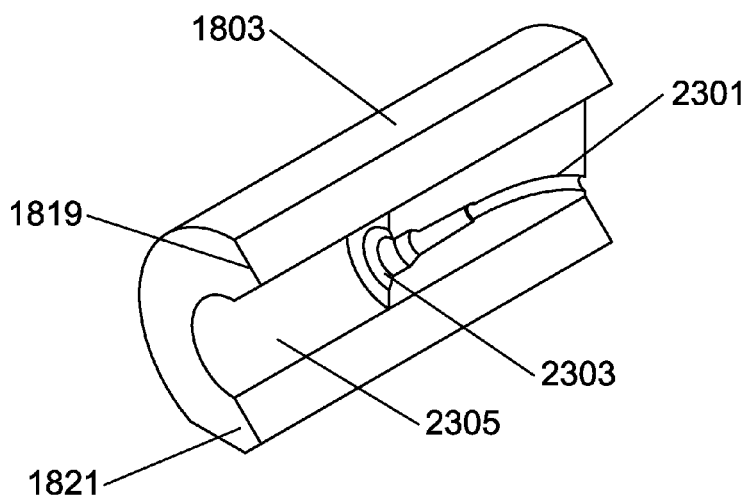
FIG. 24 is a perspective view of a first half of the shielded housing of the collimator-probe of FIG. 18.
Figures 25, 26:
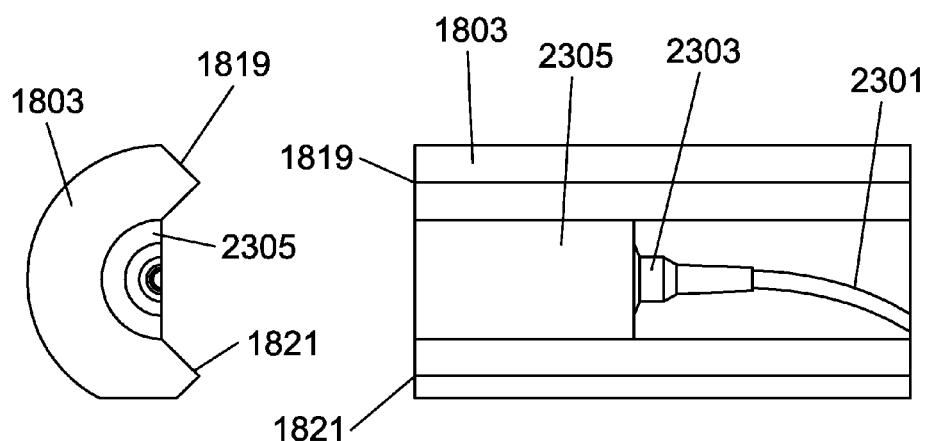
FIG. 25 is a front plan view of the first half of the shielded housing of the collimator-probe of FIG. 18.
FIG. 26 is an inside plan view of the first half of the shielded housing of the collimator-probe of FIG. 18.

FIG. 23 is an exploded view of the collimator-probe of FIG. 18 where each of the piece pans previously described can be seen in further detail. Shown is one example of the cable recess 2301 taking a curvature that travels from the recess that contains the probe itself toward the peripheral edge of the second half of the shielded housing 1803 but not entering the protrusion 1821, or in the case of the first half of the shielded housing 1801, not entering the channel 1825. Also seen in FIG. 23 is a cable termination recess 2303 as well as a probe recess 2305. These recesses are formed by casting, molding, machining, etching, or the like. The geometries of these recesses are dictated by the shape of the probe and related cable and fixturing to be contained by the shielded housing. FIG. 24 is as perspective view of a first half of the shielded housing of the collimator-probe of FIG. 18 showing some of the details previously described herein. FIG. 25 is a front plan view of the first half of the shielded housing of the collimator-probe of FIG. 18 and FIG. 26 is an inside plan view of the first half of the shielded housing of the collimator-probe of FIG. 18.

Figure 27:
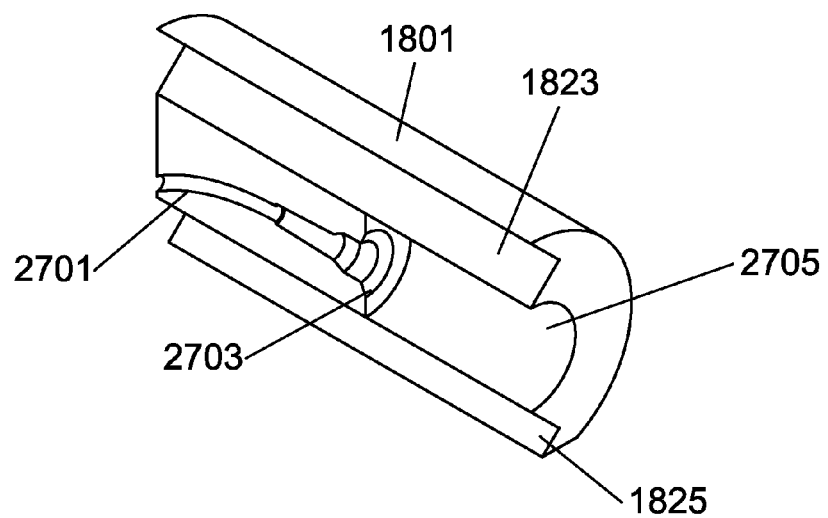
FIG. 27 is a perspective view of a second half of the shielded housing of the collimator-probe of FIG. 18.
Figures 28, 29:
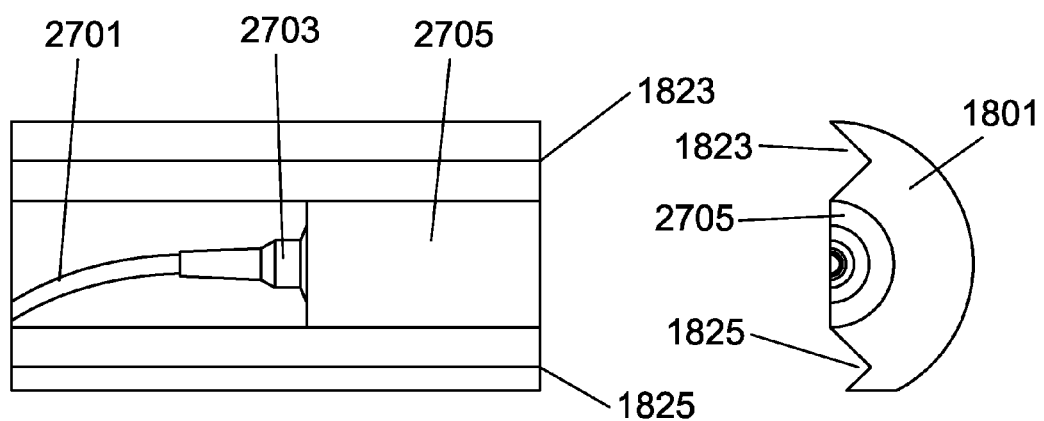
FIG. 28 is a front plan view of the second half of the shielded housing of the collimator-probe of FIG. 18.
FIG. 29 is an inside plan view of the second half of the shielded housing of the collimator-probe of FIG. 18.

FIG. 27 is a perspective view of a second half of the shielded housing 1803 of the collimator-probe of FIG. 18 also showing some of the details previously described herein. Features in this second half of the shielded housing 1803 such as the cable recess 2701, cable termination recess 2703 and probe recess 2705 being the second half of those features in the first half of the shielded housing 1801 such as the cable recess 2301, cable termination recess 2303 and probe recess 2305 that are described by way of FIG. 23. FIG. 28 is a front plan view of the second half of the shielded housing of the collimator-probe of FIG. 18 and FIG. 29 is an inside plan view of the second half of the shielded housing of the collimator-probe of FIG. 18.

While the systems and methods disclosed herein are described as being applied to nuclear power plant pipes, they are equally applicable to other conduits and vessels, as well as uses such as medical applications to determine, for example, vessel thickness, occlusion, scarring, or the like in humans and animals.

It is, therefore, apparent that there has been provided, in accordance with the various objects of the present invention, a System and Method For Determining The Radiological Composition of Material Layers Within a Conduit.

While the various objects of this invention have been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of this specification, claims and drawings appended herein.

What is claimed is:

1. A system for determining the radiological composition of material layers within a conduit, the system comprising:
    a collimator-probe comprising a probe contained within a collimator;
    a spectrometer operatively connected to the probe;
    a phantom setup comprising a vessel containing a reactor water test standard, a plurality of removable plates, a removable nuclear insulation layer, and a collimator probe attachment point; and
    a semi-logarithmic plot of spectrometer readings taken with various geometries of removable plates.

2. The system of claim 1, wherein the probe is a cadmium zinc telluride probe.

3. The system of claim 1, wherein the collimator comprises a generally cylindrical shield made from a high density material that surrounds the probe.

4. The system of claim 3, further comprising a grid attached to an opening in the collimator.

5. The system of claim 4, wherein the grid comprises a matrix of lead plates aligned to create a plurality of openings.

6. The system of claim 3, wherein the generally cylindrical shield comprises a first half and a second half.

7. The system of claim 3, wherein the high density material is selected from the group consisting of lead, tungsten, and depleted uranium.

8. The system of claim 1, further comprising a computer having a processor, memory and computer readable media, the computer configured to compare the semi-logarithmic plot of spectrometer readings stored on the computer readable media with spectrometer field readings stored on the computer readable media.

9. The system of claim 1, wherein the collimator is made from a high density material and covered with a layer of copper.

10. The system of claim 9, further comprising a layer of cadmium between the high density material and the layer of copper.

11. The system of claim 10, wherein the layer of cadmium is placed between the high density material and the layer of copper on the inner surface of the collimator.

12. The system for determining the radiological composition of material layers within a conduit of claim 1, wherein the collimator-probe comprises:
    a generally cylindrical shield comprising a high density material to contain the probe;
    the probe having a sensing face and placed within the generally cylindrical shield;
    an opening within a face of the generally cylindrical shield containing a grid of high density material to prevent low energy lateral photons from hitting the sensing face of the probe; and
    a removable cover comprising a high density material that is removably attached to the generally cylindrical shield to allow placement of the probe within the generally cylindrical shield.

13. The collimator-probe of claim 12, further comprising a spacer fitted to the shielded housing to keep the probe contained within the shielded housing a constant distance front the opening.

14. The collimator-probe of claim 12, further comprising a probe retainer placed between the probe and an interior wall of the generally cylindrical shield.

15. The system for determining the radiological composition of material layers within a conduit of claim 1, wherein the collimator-probe comprises:
    a generally cylindrical shield comprising a first half made from a high density material and a second half made from a high density material wherein the first half has protrusions that mate with channels of the second half;
    the probe having a sensing face and placed within the generally cylindrical shield; and
    an opening within a face of the generally cylindrical shield containing a grid of high density material to prevent low energy lateral photons from hitting the sensing face of the probe.

16. The collimator-probe of claim 15, further comprising a spacer fitted to the shielded housing to keep the probe contained within the shielded housing a constant distance from the opening.

17. A method of determining the radiological composition of a corrosion layer within a pipe using a system including a collimator-probe comprising a probe contained within a collimator; a spectrometer operatively connected to the probe; a phantom setup comprising a vessel containing a reactor water test standard, a plurality of removable plates, a removable nuclear insulation layer, and a collimator probe attachment point; and a semi-logarithmic plot of spectrometer readings taken with various geometries of removable plates, the method comprising the steps of:
    providing the wall thickness of a pipe being tested;
    taking readings of the pipe being tested with said collimator-probe;
    comparing the readings of the pipe being tested to said semi-logarithmic plot; and
    providing sediment layer values.

18. The method of claim 17, further comprising the step of determining the detriment of corrosion layer.

19. The method of claim 18, further comprising the step of determining the source of the detriment.

* * * * *